(12) United States Patent
Baggen et al.

(10) Patent No.: US 9,456,771 B2
(45) Date of Patent: Oct. 4, 2016

(54) METHOD FOR ESTIMATING VELOCITIES AND/OR DISPLACEMENTS FROM ACCELEROMETER MEASUREMENT SAMPLES

(75) Inventors: Constant Paul Marie Jozef Baggen, Eindhoven (NL); Ningjiang Chen, Shanghai (CN)

(73) Assignee: KONIKLIJKE PHILIPS N.V., Eindhoven (NL)

( * ) Notice: Subject to any disclaimer, the term of this patent is extended or adjusted under 35 U.S.C. 154(b) by 663 days.

(21) Appl. No.: 13/510,408

(22) PCT Filed: Nov. 22, 2010

(86) PCT No.: PCT/IB2010/055319
§ 371 (c)(1),
(2), (4) Date: May 17, 2012

(87) PCT Pub. No.: WO2011/064705
PCT Pub. Date: Jun. 3, 2011

(65) Prior Publication Data
US 2012/0232823 A1 Sep. 13, 2012

(30) Foreign Application Priority Data
Nov. 25, 2009 (CN) .......................... 2009 1 0226557

(51) Int. Cl.
*A61B 5/11* (2006.01)
*G08B 21/04* (2006.01)
(Continued)

(52) U.S. Cl.
CPC ................ *A61B 5/1117* (2013.01); *G01P 7/00* (2013.01); *G01P 15/0891* (2013.01); *G01P 15/18* (2013.01); *G08B 21/043* (2013.01); *G08B 21/0446* (2013.01); *A61B 2562/0219* (2013.01)

(58) Field of Classification Search
CPC .......... G01P 13/00; G01P 15/00; G01P 7/00; G01P 15/18; A61B 2562/0219; G08B 21/0446

USPC .................................................. 702/141, 149
See application file for complete search history.

(56) References Cited

U.S. PATENT DOCUMENTS 6,954,698 B2 * 10/2005 Tryggvason ...................... 702/5
2002/0116147 A1 * 8/2002 Vock et al. .................. 702/182
(Continued)

FOREIGN PATENT DOCUMENTS

EP        1974662      10/2008
WO   WO-2009/138900   * 11/2009
(Continued)

OTHER PUBLICATIONS

A.K. Bourke et al, "The Identification of Vertical Velocity profiles Using an Inertial Sensor to Investigate Pre-Impact Detection of Falls", ScienceDirect, Medical Engineering & Physics 30 (2008) 937-946.*
(Continued)

*Primary Examiner* — Mohamed Charioui
*Assistant Examiner* — Catherine Rastovski

(57) ABSTRACT

A fall detector includes an accelerometer for producing a time series of measurement samples representing the acceleration acting on the fall detector; a processor for estimating a vertical velocity and/or displacement of the fall detector from the measurement samples and using the estimated vertical velocity and/or displacement to determine whether the user has suffered a fall. The processor is configured to estimate a vertical velocity and/or displacement of the fall detector by estimating a corresponding time series of unit vectors representing acceleration due to gravity in the reference frame of the accelerometer from the time series of measurement samples; projecting each measurement sample onto the corresponding unit vector and subtracting acceleration due to gravity to give a series of estimates for the vertical acceleration of the fall detector; and integrating the series of estimates to give a time series of values for the vertical velocity and/or displacement of the fall detector.

16 Claims, 4 Drawing Sheets

(51) Int. Cl.
*G01P 7/00* (2006.01)
*G01P 15/08* (2006.01)
*G01P 15/18* (2013.01)

(56) References Cited

U.S. PATENT DOCUMENTS

| | | |
|---|---|---|
| 2003/0109258 A1* | 6/2003 | Mantyjarvi et al. ........... 455/440 |
| 2003/0183423 A1* | 10/2003 | Brazil et al. .................... 175/61 |
| 2006/0236761 A1 | 10/2006 | Inoue et al. |
| 2006/0255139 A1* | 11/2006 | Lee et al. ....................... 235/439 |
| 2006/0282021 A1* | 12/2006 | DeVaul et al. ................. 600/595 |
| 2007/0030159 A1* | 2/2007 | Stoev et al. ................... 340/669 |
| 2007/0030587 A1 | 2/2007 | Noda et al. |
| 2009/0168929 A1* | 7/2009 | Liu et al. ....................... 375/346 |
| 2011/0144542 A1 | 6/2011 | Jin et al. |

FOREIGN PATENT DOCUMENTS

WO WO 2009/138900 * 11/2009
WO WO2009138900 11/2009

OTHER PUBLICATIONS

A.K. Bourke et al, "Fall-Detection Through Vertical Velocity Thresholding Using a Tri-Axial Accelerometer Characterized Using an Optical Motion-Capture System", 30th Annual Int. IEEE EMBS Conf., Vancouver, BC, Canada, Aug. 20-24, 2008, pp. 2832-2835.*
A.K. Bourke et al., "The Identification of Vertical Velocity profiles Using an Inertial Sensor to Investigate Pre-impact Detection of Falls", ScienceDirect, Medical Engineering & Physics 30 (2008) 937-946.
Ge Wu, "Distinguishing Fall Activities From Normal Activities by Velocity Characteristics", Journal of Biomechanics, vol. 33, 2000, p. 1497-1500.
Bianchi et al: "Falls Event Detection Using Triaxial Accelerometry"; 31st Annual International Conference of the IEEE EMBS, Minneapolis, Minnesota, Sep. 2-6, 2009, pp. 6111-6114.
Tao et al: "Fall Incidents Detection for Intelligent Video Surveillance"; IEEE, 2005, pp. 1-5.

* cited by examiner

METHOD FOR ESTIMATING VELOCITIES AND/OR DISPLACEMENTS FROM ACCELEROMETER MEASUREMENT SAMPLES

TECHNICAL FIELD

The invention relates to a method for estimating velocities and displacements from measurement samples from an accelerometer, and in particular to a method for estimating vertical velocities and vertical displacements that can be used in detecting falls by a user.

BACKGROUND

Falls affect millions of people each year and result in significant injuries, particularly among the elderly. In fact, it has been estimated that falls are one of the top three causes of death in elderly people. A fall can be defined as a sudden, uncontrolled and unintentional downward displacement of the body to the ground followed by an impact.

Personal Help Buttons (PHBs) are available that require the user to push the button to summon help in an emergency. However, if the user suffers a severe fall (for example if they are knocked unconscious), the user might be unable to push the button, which might mean that help doesn't arrive for a significant period of time, particularly if the user lives alone.

Fall detectors are also available that process the output of one or more movement sensors to determine if the user has suffered a fall. However, it has been found that these fall detectors have an unfavorable trade-off between fall detection probability and false alarm rate.

Given that a high false alarm rate will result in additional costs to the organization responsible for giving assistance to the user of the fall detector (i.e. they will need to contact or visit the user of the fall detector when the fall detection alarm is triggered) and that a high false alarm rate is undesirable for the user of the fall detector, it has been found that an economically viable fall detector should provide a false alarm rate of, say, less than one false alarm in each two-month period, while maintaining a (positive) fall detection probability above 95 percent.

Most existing body-worn fall detectors make use of an accelerometer (usually a 3D accelerometer that measures acceleration in three dimensions) and they try to infer the occurrence of a fall by processing the time series generated by the accelerometer.

In particular, a fall detector can estimate a velocity and/or displacement for the fall detector from the accelerometer measurement samples and use these features (along with other features derived from the accelerometer measurement samples) to determine whether the user of the fall detector has suffered a fall.

It is desirable to provide fall detectors in the form of pendants that can be worn around a user's neck and that is otherwise free to move relative to the user; as such fall detectors are lightweight and unobtrusive in use. However, existing methods for estimating the vertical velocity and vertical displacement do not provide sufficiently accurate estimates when applied to measurement samples obtained from an accelerometer in this type of fall detector.

Therefore, there is a need for an improved method for estimating vertical velocities and/or vertical displacements from accelerometer measurement samples.

SUMMARY

According to a first aspect, there is provided a fall detector for use in detecting falls by a user, the fall detector comprising an accelerometer for producing a time series of measurement samples representing the acceleration acting on the fall detector; a processor for estimating a vertical velocity and/or vertical displacement of the fall detector from the measurement samples and using the estimated vertical velocity and/or vertical displacement to determine whether the user has suffered a fall; wherein the processor is configured to estimate a vertical velocity and/or vertical displacement of the fall detector from the measurement samples by estimating a corresponding time series of unit vectors representing acceleration due to gravity in the reference frame of the accelerometer from the time series of measurement samples; projecting each measurement sample onto the corresponding unit vector and subtracting acceleration due to gravity to give a series of estimates for the vertical acceleration of the fall detector; and integrating the series of estimates for the vertical acceleration over a time period to give a time series of values for the vertical velocity and/or vertical displacement of the fall detector.

According to a second aspect, there is provided a method of estimating a vertical velocity and/or vertical displacement of an object comprising an accelerometer, the method comprising obtaining a time series of measurement samples from the accelerometer representing the acceleration acting on the object; estimating a corresponding time series of unit vectors representing acceleration due to gravity in the reference frame of the accelerometer from the time series of measurement samples; projecting each measurement sample onto the corresponding unit vector and subtracting acceleration due to gravity to give a series of estimates for the vertical acceleration of the object; and integrating the series of estimates for the vertical acceleration over a time period to give a time series of values for the vertical velocity and/or vertical displacement of the object.

According to a third aspect, there is provided a method for use in detecting falls by a user of a fall detector comprising an accelerometer, the method comprising estimating a vertical velocity and/or vertical displacement from measurement samples from the accelerometer as described above and using the estimated vertical velocity and/or vertical displacement to determine whether the user has suffered a fall.

According to a fourth aspect, there is provided a computer program product comprising computer program code that, when executed on a suitable computer or processor, is configured to cause the computer or processor to perform either of the methods described above.

BRIEF DESCRIPTION OF THE DRAWINGS

Exemplary embodiments of the invention will now be described, by way of example only, with reference to the following drawings, in which.

DETAILED DESCRIPTION OF THE PREFERRED EMBODIMENTS

Figure 1:
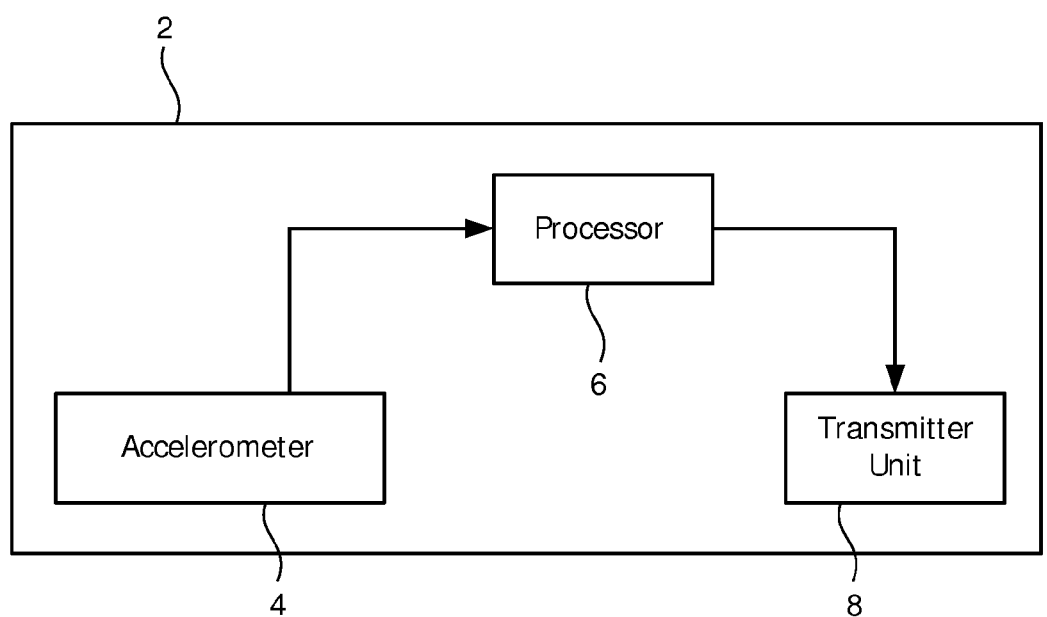
FIG. 1 is a block diagram of a fall detector suitable for implementing the method in accordance with the invention.

A fall detector 2 capable of implementing the method according to the invention is shown in FIG. 1. The fall detector 2 is designed in the form of a pendant to be worn around the neck of a user that does not adversely affect the movement or balance of the user.

In this exemplary embodiment, the fall detector 2 comprises an accelerometer 4 (in particular a 3D accelerometer that provides measurements of the acceleration along the three orthogonal measurement axes of the accelerometer 4) which is connected to a processor 6. The processor 6 receives measurement samples from the accelerometer 4 and processes the measurement samples to estimate the vertical velocity of the fall detector 2 and/or the vertical displacement of the fall detector 2 over various time periods. The processor 6 uses the vertical velocity and/or vertical displacement (usually in connection with other features derived from the accelerometer measurement samples) to determine whether the user has fallen.

The fall detector 2 also comprises a transmitter unit 8 that allows the fall detector 2 to transmit an alarm signal to a base station associated with the fall detector 2 (which can then issue an alarm or summon help from a healthcare provider or the emergency services) or directly to a remote station (for example located in call centre of a healthcare provider) if a fall is detected, so that assistance can be summoned for the user.

In some embodiments (not represented by the fall detector shown in FIG. 1), the fall detector 2 can further comprise other sensors in addition to the accelerometer, such as a pressure sensor, magnetometer and/or gyroscope. The fall detector 2 may also comprise an audible alarm unit that can be activated by the processor 6 in the event that the processor 6 determines that the user has suffered a fall. The fall detector 2 may also be provided with a button that allows the user to manually activate the audible alarm unit if they require assistance (or deactivate the alarm if assistance is not required).

Figure 2:
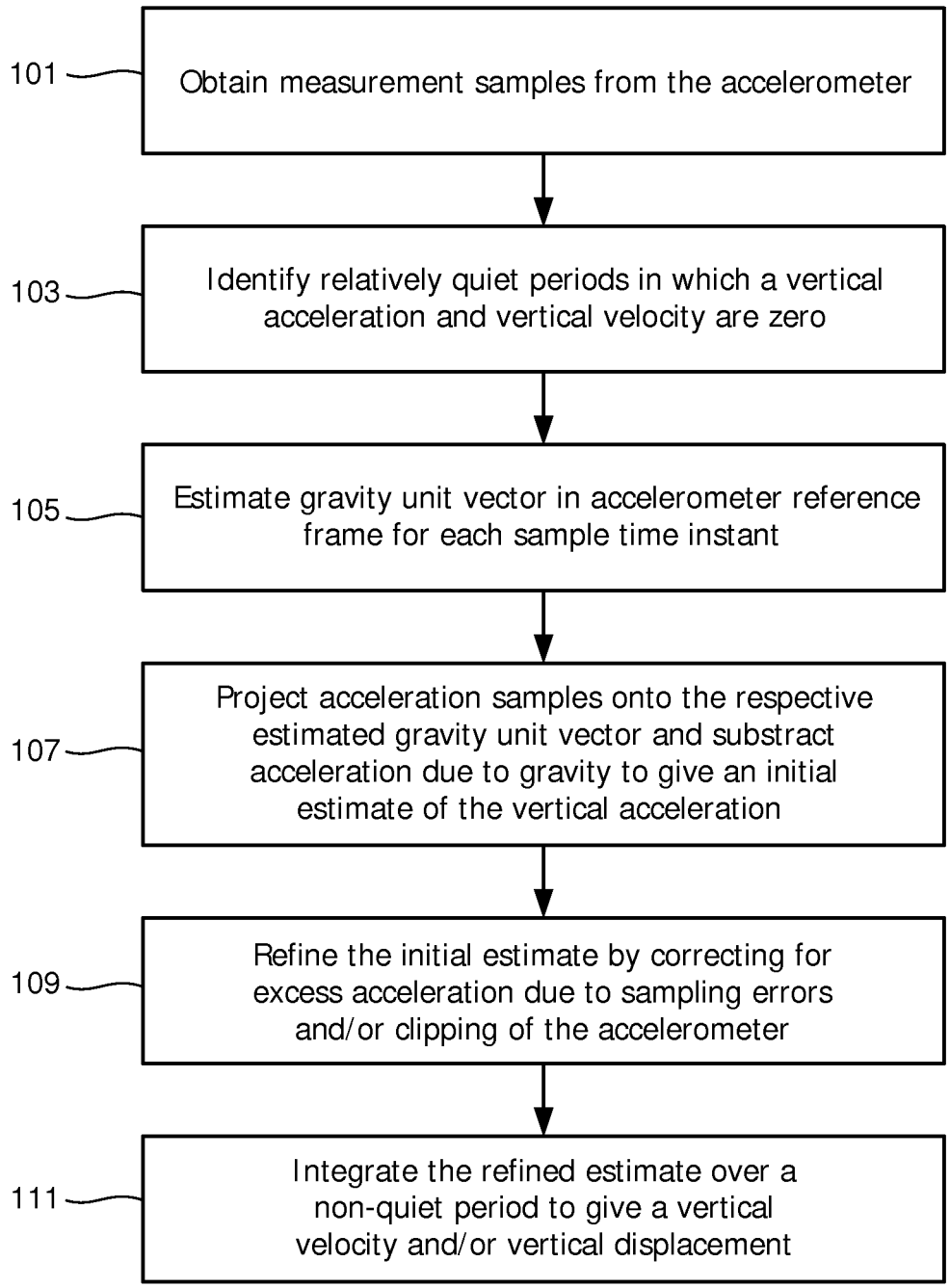
FIG. 2 is a flow chart illustrating a method in accordance with the invention.

The method is illustrated in FIG. 2. In step 101, a time series of measurement samples are obtained from the accelerometer 4. Each measurement sample is a three-dimensional vector representing the measured acceleration in the reference frame of the accelerometer 4. Subsequent steps in the method operate on these measurement samples to obtain an estimate of the vertical velocity and/or vertical displacement (in a global reference frame) during falls.

In step 103, 'relatively quiet' periods in the measurement samples are identified in which the vertical acceleration and vertical velocity are approximately zero. The end point of a 'relatively quiet' period and the start point of the next 'relatively quiet' period provide boundary values for the estimation of the vertical velocity and/or vertical displacement later in the method.

As a fall is unlikely to have occurred during a 'relatively quiet' period, it is not necessary to continue with the method shown in FIG. 2 for the measurement samples within that period, so the method returns to step 101, until a 'non-quiet' period is identified (i.e. a period in which the vertical acceleration and/or vertical velocity are substantially non-zero).

A preferred implementation of step 103 is described in more detail below with reference to FIG. 3.

Figure 3:
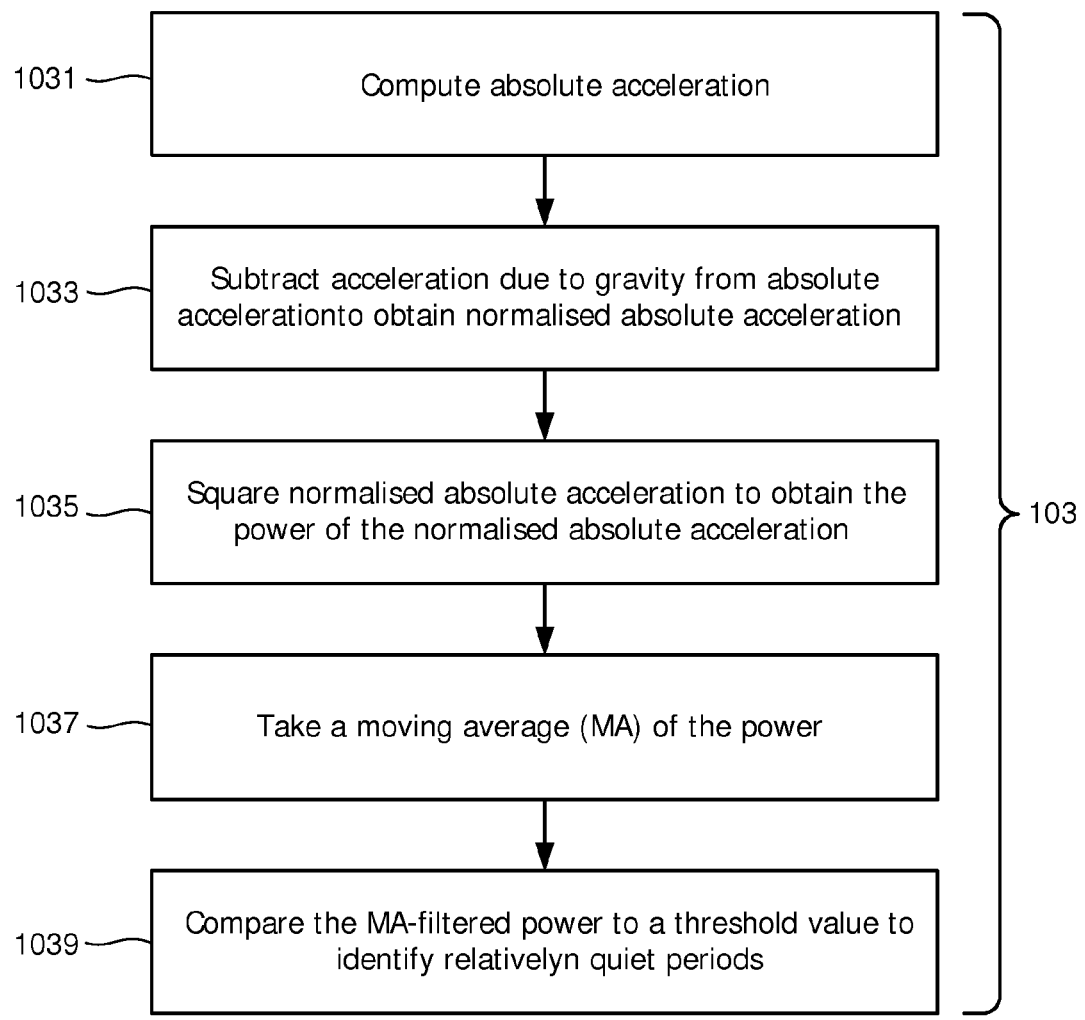
FIG. 3 illustrates step 103 of the flow chart in FIG. 2 in more detail.

Thus, in step 1031 of FIG. 3, the absolute acceleration is computed for each measurement sample by taking the square root of the sum of the squares of the three components of the sample:

$$a_{absolute} = \sqrt{(a_x^2 + a_y^2 + a_z^2)} \quad (1)$$

where $a_x$, $a_y$ and $a_z$ are the components of the acceleration along each of the measurement axes of the accelerometer 4.

In step 1033, acceleration due to gravity (9.81 ms$^{-2}$) is subtracted from the absolute acceleration to obtain a normalized absolute acceleration.

The normalized absolute acceleration is squared to obtain the power of the normalized absolute acceleration (step 1035) and a moving average (MA) of the power of the normalized absolute acceleration is taken to obtain an MA-filtered power of the normalized absolute acceleration (step 1037). In the preferred embodiment, the duration of the MA filter is 0.5 seconds.

In step 1039, the MA-filtered power of the normalized absolute acceleration is compared with a non-zero threshold value to identify the sample times that are relatively quiet. For example, if in a two-second interval the value of the MA-filtered power is less than 10, the middle of the interval can be defined as 'relatively quiet'. Those skilled in the art will be able to select an appropriate value for the threshold, bearing in mind that an acceleration of 1 g would result in a value for the MA-filtered power of around 100.

Returning now to the method in FIG. 2, in step 105, a unit vector representing acceleration due to gravity in the reference frame of the accelerometer 4 is estimated for each measurement sample outside of the 'relatively quiet' periods. This step is described in more detail below with reference to FIG. 4. The resulting time series of unit vectors is used in the next step of the method to identify the components of the acceleration measured by the accelerometer in the vertical direction.

Figure 4:
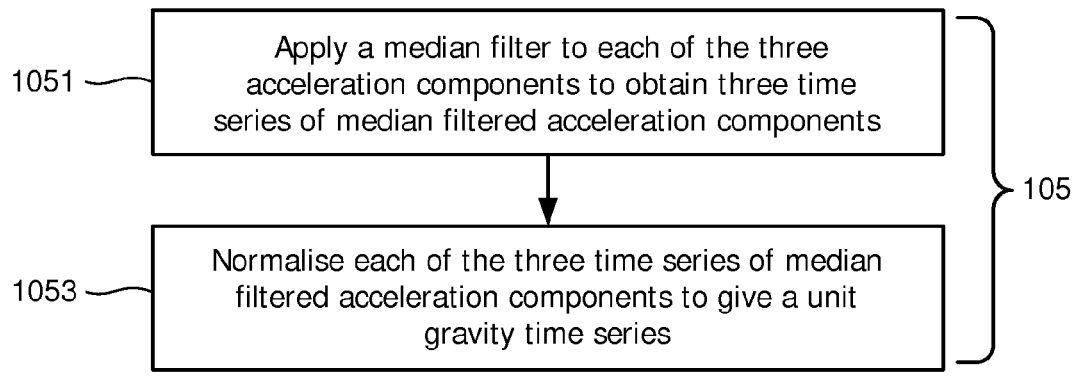
FIG. 4 illustrates step 105 of the flow chart in FIG. 2 in more detail.

Thus, in step 1051 of FIG. 4, a median filter is applied to each of the three acceleration components in each measurement sample to obtain three time series of median-filtered acceleration components. In a preferred embodiment, the duration of the median filter is 0.5 seconds.

Then, in step 1053, a unit gravity time series is computed by normalizing the length of each of the median-filtered acceleration components at each sampling time using an absolute value derived from each of the three median-filtered acceleration components at that sample time. Thus, the gravity unit vector $\hat{g}$ in the reference frame of the accelerometer 4 at a sampling time t is given by:

$$\hat{g} = [\hat{g}_x, \hat{g}_y, \hat{g}_z] = \left[ \frac{a_{xmf}^2}{\sqrt{(a_{xmf}^2 + a_{ymf}^2 + a_{zmf}^2)}}, \frac{a_{ymf}^2}{\sqrt{(a_{xmf}^2 + a_{ymf}^2 + a_{zmf}^2)}}, \frac{a_{zmf}^2}{\sqrt{(a_{xmf}^2 + a_{ymf}^2 + a_{zmf}^2)}} \right] \quad (2)$$

where $a_{xmf}$, $a_{ymf}$ and $a_{zmf}$ are the median filtered acceleration components of the measurement sample at time t.

Returning again to FIG. 2, each acceleration measurement sample is projected onto its respective unit gravity vector (step 107). That is, a measurement sample obtained for a time t is projected onto the gravity unit vector determined for the sample at time t.

As those skilled in the art will appreciate, the projection of the acceleration measurement sample a onto the gravity unit vector $\hat{g}$ gives a scalar value $a_v$ representing the magnitude of the acceleration in a vertical direction. The projection can be expressed as:

$$a_v = (a \cdot \hat{g}) \quad (3)$$

Acceleration due to gravity (i.e. 9.81 ms$^{-2}$) is then subtracted from the acceleration in the vertical direction to give an initial estimate of the vertical acceleration of the fall detector 2.

Then, in step 109, the initial estimate of the vertical acceleration is refined by correcting for excess acceleration due to sampling errors and/or clipping of the measurements made by the accelerometer 4. Sampling errors and/or clipping can occur, for example, when an impact occurs, so the initial measurement samples from the accelerometer 4 are less reliable or accurate at these times.

Some assumptions can be made at this stage to correct the initial estimate of the vertical acceleration for excesses due to sampling errors and/or clipping in each 'non-quiet' period (i.e. a period between two 'relatively quiet' periods).

Firstly, during the 'relatively quiet' periods, the vertical acceleration and the vertical velocity are both assumed to be zero. Therefore, at the beginning and end of each 'non-quiet' period, the vertical velocity will be zero. This assumption implies that the integral of the vertical acceleration over each 'non-quiet' period should also be zero.

Thus, in the event that the integral of the initial measurement sample estimates of the vertical acceleration over the 'non-quiet' period is not zero (the non-zero amount being denoted the excess vertical acceleration), the excess vertical acceleration is divided across each of the initial measurement sample estimates in the 'non-quiet' period to correct the initial estimate of the vertical acceleration. After correction, the integral of the corrected measurement sample estimates of the vertical accelerations over the 'non-quiet' period should be zero.

It has been found that the measurement samples having the largest absolute value of vertical acceleration are most likely to deviate because of clipping and/or sampling errors (and those samples are likely to correspond to an impact) and contribute most to the excess vertical acceleration. Therefore, the excess vertical acceleration in the initial measurement sample estimates is preferably corrected proportionally according to the locally computed "filtered impact".

This proportional correction is applied by (i) computing the absolute value of the measurement sample estimates of the vertical acceleration in the 'non-quiet' period, (ii) determining the sum of the absolute values in the 'non-quiet' period and (iii) dividing the excess acceleration among the initial measurement sample estimates of the vertical acceleration in the 'non-quiet' period, where each measurement sample estimate obtains a fraction of its absolute value divided by said sum of the absolute values. In one embodiment, the fraction of the excess acceleration attributed to initial measurement sample estimate i is given by $$\frac{\text{impact\_filt}(i)}{\sum_{i-n}^{i+n} (\text{impact\_filt}(i))} \quad (4)$$

where impact_filt(i) is the average filtered normalized absolute acceleration for the i-th initial measurement sample estimate and n is an integer. For a fall, the non-quiet period is generally in the range of a second or a few seconds, and with a sampling frequency of 50 Hz, n will be of the order of 50 to 100. This correction results in the refined estimate of the vertical acceleration.

Finally, in step 111, the refined estimate of the vertical acceleration is integrated over a 'non-quiet' period to give a time series of values for the vertical velocity and/or twice integrated over the 'non-quiet' period to give a time series of values for the vertical displacement.

When integrating vertical acceleration to arrive at vertical velocity, the integration is usually performed over a short period using a rectangular integration window (a Dirichlet window). However, it has been found that such an integration window leads to velocity estimates that are extremely sensitive to previous accelerations that shift out of the window.

Figure 5:
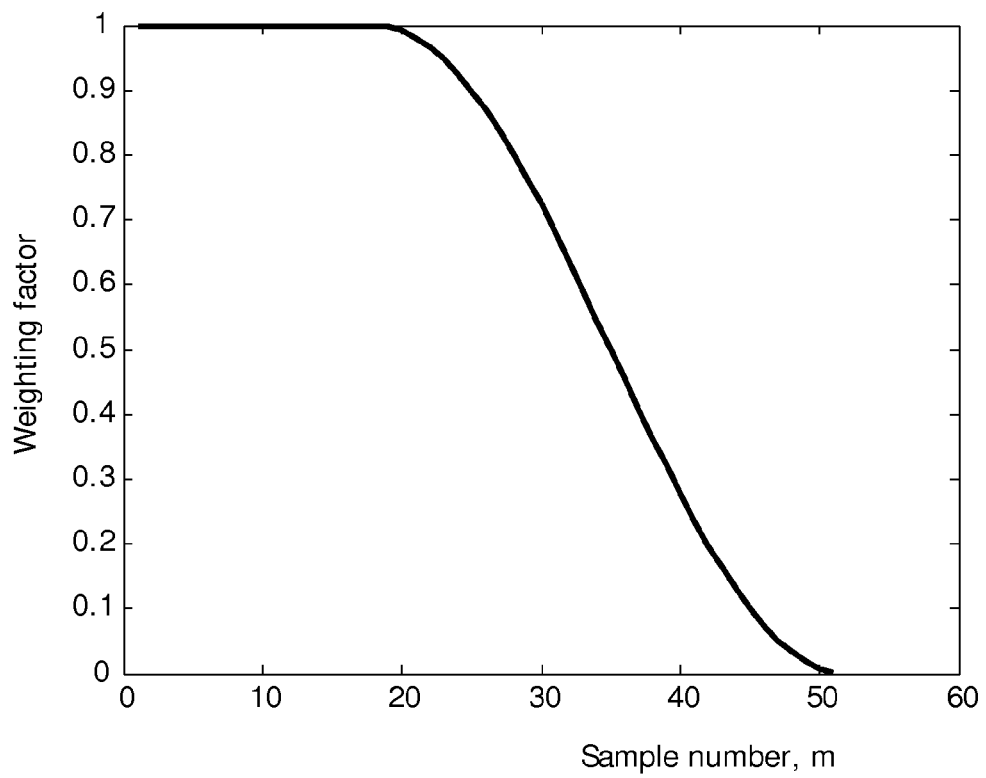
FIG. 5 is a graph illustrating an integration window that can be used to integrate vertical acceleration into vertical velocity in accordance with an embodiment of the invention.

In order to mitigate this problem, a non-rectangular integration window is used, for example as shown in FIG. 5. In this window, the estimated vertical velocity is determined from a weighted sum of the M most recent estimates of the vertical acceleration, where the weighting decreases as estimates get older. In this embodiment, M is 50. Thus, it can be seen in FIG. 5 that the most recent estimates (roughly the most recent 16 samples from 50) are weighted with weighting factor 1, which corresponds to pure integration. However, estimates older than this (samples with index 17 to 50 in the past) have a weighting factor that is less than 1 so that they contribute less to the estimate for the vertical velocity. In particular, acceleration estimates leaving the filter have little impact on the variations of the estimated velocity. In the preferred embodiment illustrated in FIG. 5, a raised cosine window (also known as a Hann window) is used.

A similar type of window is also used for calculating the vertical displacement.

The determined vertical velocity and/or vertical displacement can be used by the fall detector 2, possibly in conjunction with values for other features that are characteristic of a fall to determine whether the user of the fall detector 2 has suffered a fall. The fall detector 2 may also determine values for other features from the determined vertical velocity and/or vertical displacement themselves. For example, if the user has suffered a fall, there is likely to be a minimum vertical velocity of $-1.3\ \text{ms}^{-1}$ (i.e. $1.3\ \text{ms}^{-1}$ downwards), and the fall detector 2 can use a local minimum in the vertical velocity to identify a point at which a fall has occurred.

Although the method provides significant improvements in the estimation of vertical velocities and/or vertical displacements in pendant-type fall detectors (i.e. fall detectors that can move relatively freely when worn by the user), it will be appreciated that the method can also provide improvements in the estimation of vertical velocities and vertical displacements in other types of fall detector, such as those worn on a user's wrist, at their waist, on their chest or on their back.

In addition, although it has been described above that the processor 6 in the fall detector 2 determines the vertical velocity and/or vertical displacement from the measurement samples from the accelerometer 4, it will be appreciated that in alternative embodiments the transmitter unit 8 can be used to transmit the measurement samples from the accelerometer 4 to the base station or remote station, and the vertical velocity and/or vertical displacement can be determined in the base station or remote station. The base station or remote station can also carry out the processing to determine whether the user has suffered a fall.

There is therefore provided an improved method for determining vertical velocities and vertical displacements from accelerometer measurement samples.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A fall detector for detecting falls by a user, the fall detector comprising:
   an accelerometer for producing a time series of measurement samples representing the acceleration acting on the fall detector;
   a transmitter for transmitting an alarm signal to summon assistance;
   a processor for estimating a vertical velocity and/or vertical displacement of the fall detector from the measurement samples and using the estimated vertical velocity and/or vertical displacement to determine whether the user has suffered a fall; wherein the processor is configured to estimate a vertical velocity and/or vertical displacement of the fall detector from the measurement samples by:
   estimating a corresponding time series of unit vectors representing acceleration due to gravity in a reference frame of the accelerometer from the time series of measurement samples;
   projecting each measurement sample onto the corresponding unit vector and subtracting acceleration due to gravity to give a series of estimates for the vertical acceleration of the fall detector;
   after projecting each measurement sample onto the corresponding unit vector and subtracting acceleration due to gravity to give the series of estimates for the vertical acceleration of the fall detector, correcting the series of estimates to correct for excess acceleration due to sampling errors and/or clipping in the measurement samples including dividing the excess vertical acceleration across each of the series of estimates of the vertical acceleration in said time period to generate a corrected series of estimates of the vertical acceleration;
   integrating the corrected series of estimates for the vertical acceleration to give a time series of values for the vertical velocity and/or vertical displacement of the fall detector,
   from the time series of values for the vertical velocity and/or vertical displacement, determining whether the user has fallen, and
   in response to determining that the user has fallen, causing the transmitter to transmit the alarm signal to summon assistance.

2. The fall detector as claimed in claim 1, wherein the processor is configured to integrate the series of estimates for the vertical acceleration over a time period during which the vertical acceleration and vertical velocity of the fall detector are non-zero to give the time series of values for the vertical velocity and/or vertical displacement of the fall detector.

3. The fall detector as claimed in claim 2, wherein the processor is configured to identify time periods during which the vertical acceleration and vertical velocity of the fall detector are non-zero by:
   computing an absolute acceleration value for each measurement sample in the time series;
   subtracting acceleration due to gravity from each of the computed acceleration absolute values to obtain a time series of normalized absolute accelerations;
   squaring each of the normalized absolute accelerations to obtain a time series representing a power of the normalized absolute accelerations;
   taking a moving average of the time series representing the power of the normalized absolute acceleration; and
   comparing the moving average of the time series representing the power of the normalized absolute acceleration with a non-zero threshold value to identify said time periods.

4. The fall detector as claimed in claim 1, wherein each measurement sample comprises three acceleration components, and wherein the processor is configured to estimate a corresponding time series of unit vectors representing acceleration due to gravity in a reference frame of the accelerometer from the time series of measurement samples by:
   applying a median filter to each of the three acceleration components to obtain respective time series of median filtered components; and
   normalizing a length of each of the components in the respective time series to give the time series of unit vectors representing acceleration due to gravity.

5. The fall detector as claimed in claim 1, wherein the processor is configured to refine the series of estimates to correct for excess acceleration due to sampling errors and/or clipping in the measurement samples that occur when the fall detector has an impact.

6. The fall detector as claimed in claim 1, wherein the fall detector is in the form of a pendant to be worn around the neck of the user.

7. A fall detector for use in detecting falls by a user, the fall detector comprising:
   an accelerometer configured to produce a time series of measurement samples representing acceleration acting on the fall detector;
   a transmitter configured to transmit an alarm signal to a base station;
   a processor configured to estimate a vertical velocity and/or vertical displacement of the fall detector from the measurement samples by:
   estimating a corresponding time series of unit vectors representing acceleration due to gravity in a reference frame of the accelerometer from the time series of measurement samples;
   projecting each measurement sample onto the corresponding unit vector and subtracting acceleration due to gravity to give a series of estimates for the vertical acceleration of the fall detector;
   integrating the series of estimates of the vertical acceleration in a time period in which the vertical acceleration is non-zero to generate an initial estimate of the vertical acceleration;
   when the initial estimate of the vertical acceleration is non-zero, a resulting non-zero amount being denoted an excess vertical acceleration;
   dividing the excess vertical acceleration across each of the series of estimates of the vertical acceleration in said time period to generate a series of refined estimates of the vertical acceleration;

integrating the series of refined estimates of the vertical acceleration over the time period when the vertical acceleration and vertical velocity are non-zero to give a time series of values for the vertical velocity and/or vertical displacement corrected for the excess vertical acceleration of the fall detector;

based on at least one of vertical velocity and/or the vertical displacement, determining whether the user has suffered a fall; and in response to determining that the user has suffered a fall, controlling the transmitter to transmit the alarm signal to the base station.

8. The fall detector as claimed in claim 7, wherein the processor is further configured to integrate the series of estimates for the vertical acceleration over said time period using a non-rectangular integration window to give the time series of values for the vertical velocity and/or vertical displacement of the fall detector.

9. The fall detector as claimed in claim 8, wherein the processor is configured to integrate the series of estimates for the vertical acceleration over said time period using a raised cosine integration window.

10. The fall detector as claimed in claim 7, wherein the processor is configured to divide the excess vertical acceleration across each of the estimates proportionally according to a ratio of an absolute value of each estimate of the series of estimates to the sum of the absolute values of the series of estimates.

11. The fall detector as claimed in claim 7, wherein the processor is configured to divide the excess vertical acceleration across each of the estimates proportionally by:
   computing an absolute value of each of the estimates of the vertical acceleration during said time period;
   determining a sum of the absolute acceleration values in said time period; and
   dividing the excess vertical acceleration among the estimates of the vertical acceleration in said time period where each estimate receives a fraction of its absolute value divided by the sum.

12. The fall detector as claimed in claim 7, wherein the processor is further configured to divide the excess acceleration across each estimate of the series of estimates by:
   (i) computing an absolute value corresponding to each estimate of the series of estimates in the time period,
   (ii) determining a sum of the absolute values,
   (iii) dividing the absolute value corresponding to each estimate of the series of estimates by the determined sum of the absolute values, and
   (iv) adjusting each estimate of the series of estimates based on a corresponding portion of the excess acceleration to generate the series of refined estimates, the corresponding portion being based on the corresponding computed absolute value divided by the determined sum of the absolute values.

13. A method for use in detecting falls by a user of a fall detector which includes an accelerometer, the method comprising:
   obtaining a time series of measurement samples from the accelerometer representing the acceleration acting on the fall detector;
   estimating a corresponding time series of unit vectors representing acceleration due to gravity in the reference frame of the accelerometer from the time series of measurement samples;
   projecting each measurement sample onto the corresponding unit vector and subtracting acceleration due to gravity to give a series of estimates for the vertical acceleration of the object;
   correcting the series of estimates to correct for excess acceleration due to sampling errors and/or clipping in the measured samples that occur when the fall detector has an impact including dividing the excess vertical acceleration across each estimate of the series of estimates of the vertical acceleration in said time period to generate a corrected series of estimates of the vertical acceleration;
   integrating the corrected series of estimates for the vertical acceleration over a time period to give a time series of values for the vertical velocity and/or vertical displacement of the object;
   using the estimated vertical velocity and/or vertical displacement to determine whether the user has suffered a fall;
   in response to determining that the user has suffered a fall, controlling a transmitter to transmit an alarm signal to a base station to summon help.

14. A non-transitory computer-readable medium carrying computer program code that, when executed on a suitable computer or processor, is configured to cause the computer or processor to perform the method claimed in claim 13.

15. The method as claimed in claim 13, wherein correcting the estimates includes:
   summing absolute values of the series of estimates of the vertical acceleration over said time period;
   dividing the absolute value of each estimate by the sum of the absolute values to generate a fraction corresponding to each estimate; and
   wherein the excess vertical acceleration is divided across each of the estimates of the vertical acceleration in the time period proportionally to the corresponding fraction to correct those estimates of the vertical acceleration.

16. The method as claimed in claim 13, wherein identifying time periods during which the vertical acceleration and vertical velocity of the fall detector are non-zero by:
   computing an absolute acceleration value for each measurement sample in the time series;
   subtracting acceleration due to gravity from each of the computed absolute values to obtain a time series of normalized absolute accelerations;
   squaring each of the normalized absolute accelerations to obtain a time series representing a power of the normalized absolute accelerations;
   taking a moving average of the time series representing the power of the normalized absolute acceleration; and
   comparing the moving average with a non-zero threshold value to identify said time periods, wherein the integrating is performed during said time periods.

* * * * *